United States Patent
El Fakhri et al.

(10) Patent No.: US 9,870,627 B2
(45) Date of Patent: Jan. 16, 2018

(54) SYSTEM AND METHOD FOR LIMITED ANGLE POSITRON EMISSION TOMOGRAPHY

(71) Applicant: The General Hospital Corporation, Boston, MA (US)

(72) Inventors: Georges El Fakhri, Brookline, MA (US); Quanzheng Li, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 89 days.

(21) Appl. No.: 15/095,721

(22) Filed: Apr. 11, 2016

(65) Prior Publication Data

US 2016/0300366 A1    Oct. 13, 2016

Related U.S. Application Data

(60) Provisional application No. 62/146,004, filed on Apr. 10, 2015.

(51) Int. Cl.
G06K 9/00       (2006.01)
G06T 11/00      (2006.01)
A61B 6/03       (2006.01)
A61B 6/00       (2006.01)

(52) U.S. Cl.
CPC ............ *G06T 11/003* (2013.01); *A61B 6/037* (2013.01); *A61B 6/5205* (2013.01)

(58) Field of Classification Search
None
See application file for complete search history.

(56) References Cited

U.S. PATENT DOCUMENTS

| | | | |
|---|---|---|---|
| 9,734,601 B2* | 8/2017 | Bresler | G06T 11/006 |
| 2009/0161933 A1* | 6/2009 | Chen | G06T 11/006 |
| | | | 382/131 |
| 2010/0108896 A1* | 5/2010 | Surti | G01T 1/00 |
| | | | 250/363.04 |
| 2010/0272335 A1* | 10/2010 | Hu | G06T 11/006 |
| | | | 382/131 |
| 2012/0068076 A1* | 3/2012 | Daghighian | A61B 6/037 |
| | | | 250/363.03 |
| 2012/0155729 A1* | 6/2012 | Benson | G06T 11/006 |
| | | | 382/131 |
| 2014/0270439 A1* | 9/2014 | Chen | G06T 11/006 |
| | | | 382/131 |

* cited by examiner

*Primary Examiner* — Shervin Nakhjavan
(74) *Attorney, Agent, or Firm* — Quarles & Brady LLP

(57) ABSTRACT

Described here are systems and methods for reconstructing images from limited angle positron emission tomography ("PET") data acquired using a PET system with a partial-ring detector configuration, such as an in-beam PET system. The reconstruction process is specifically designed to account for the limited angular coverage of the partial-ring detector by implementing a reduced angle system matrix in an iterative reconstruction process.

13 Claims, 2 Drawing Sheets

SYSTEM AND METHOD FOR LIMITED ANGLE POSITRON EMISSION TOMOGRAPHY

CROSS-REFERENCE TO RELATED APPLICATIONS

This application claims the benefit of U.S. Provisional Patent Application Ser. No. 62/146,004, filed on Apr. 10, 2015, and entitled "Limited Angle Positron Emission Tomography."

STATEMENT REGARDING FEDERALLY SPONSORED RESEARCH

This invention was made with government support under Grant Numbers EB001232, EB013293, CA165221 awarded by the National Institutes of Health. The government has certain rights in the invention.

BACKGROUND OF THE INVENTION

Partial-ring positron emission tomography ("PET") systems have been gaining use in breast imaging and radiation therapy applications. For breast imaging, partial-ring PET systems allow detectors to be positioned closer to the patient's anatomy, which improves sensitivity compared to full-ring detectors. Likewise, the opening in the partial-ring detector assembly allows clinician access to the patient (e.g., to perform a biopsy). Similarly, for radiation therapy applications, partial-ring PET systems provide an opening through which a treatment beam can be delivered to a patient while that patient is positioned in the imaging field-of-view of the PET system. This arrangement allows for verification of radiation beam delivery immediately after cessation of the radiation beam, and without needing to move the patient.

The limited view angle coverage associated with partial-ring detectors results in an incomplete angular view sampling, which causes artifacts in image reconstruction. Time-of-flight ("TOF") PET can be used to improve the image quality achievable with partial-ring PET systems because the number of angular views necessary for an artifact-free image reconstruction can be decreased based on the increased temporal resolution achievable with TOF PET techniques.

Thus, there remains a need for appropriate image reconstruction techniques that can allow for the benefits of TOF PET to be applied to limited angle applications.

SUMMARY OF THE INVENTION

The present invention overcomes the aforementioned drawbacks by providing a method for reconstructing an image from limited angle positron emission tomography ("PET") data. The method includes providing limited angle PET data to a computer system. This limited angle PET data indicates gamma ray activity in a subject. A reduced angle system matrix that includes rows associated with only view angles represented in the limited angle PET data is selected. The image is then iteratively reconstructed from the limited angle PET data by iteratively solving an optimization problem that includes the selected reduced angle system matrix.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
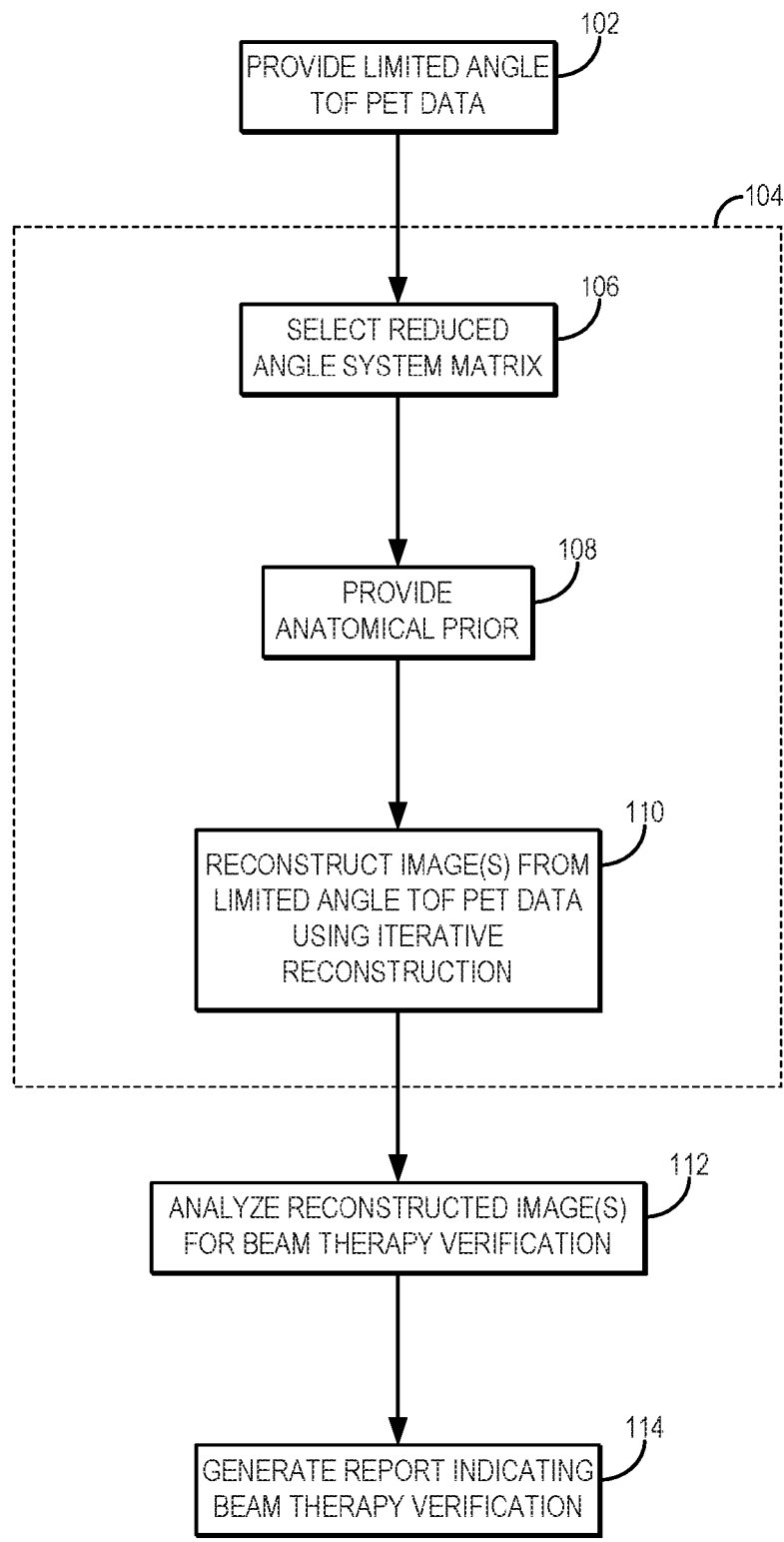
FIG. 1 is a flowchart setting forth the steps of an example method for reconstructing an image from limited angle, time-of-flight ("TOF") positron emission tomography ("PET") data acquired using a partial-ring PET system.

PET imaging can be used for the verification of hadron therapies, such as proton therapy and carbon beam therapy. Hadron therapies include aiming a beam of ionizing particles (e.g., protons, heavy ions) at a target tumor to promote cell death in the tumor. During the ion beam irradiation, positron emitters are produced on the beam path through nuclear fragmentation reactions. These positron emitters can be used as radiotracers that can be imaged with a PET scanner. Examples of positron emitters that can be generated in this process include $^{15}O$, $^{11}C$, and $^{13}N$. These radionuclide species have half-lives on the order of only a few minutes (e.g., 2-20 minutes) and thus must be imaged rapidly after their generation. Additionally, because the PET signal originates from contributions of multiple different radionuclide species with different decay rates, the verification of proton therapy with PET imaging is very sensitive to the timing of the data acquisition.

Dedicated PET detectors can be integrated into beam delivery systems for the PET verification of proton therapy. One advantage of the in-beam system configuration is the time course of PET acquisitions. For cyclotron based facilities, where the beam is delivered continuously during the treatment, PET acquisition can be started immediately following the treatment, which minimizes the delay between treatment and PET acquisition. For synchrotron based facilities, where a pulsed beam is delivered, PET data can be collected during the times in which beam delivery is paused.

Because of the timely data acquisition provided by in-beam system configurations, the PET activity level in the subject's tissues is at a high level for both long half-life (e.g., $^{11}C$, $^{13}N$) and short half-life (e.g., $^{15}O$, $^{10}C$) radionuclide species. As a result, the effect of biological washout of PET activities is minimized. As another advantage, patient repositioning errors and anatomical morphologic changes can also be avoided or minimized with the in-beam system configuration because data are acquired with the subject still at the treatment position.

However, integration of a dedicated PET imaging system into the beam delivery system is technically demanding. One significant technical challenge is the geometric constraints on the PET imaging system in the treatment environment. For example, a conventional full-ring detector is not feasible because an opening for the beam portal and flexible patient positioning is needed. Thus, a partial-ring detector is needed; however, the use of partial-ring detectors results in incomplete angular data collection, which results in lower sensitivity, limited field-of-views, and artifacts in the reconstructed images.

Described here are systems and methods that address the technical challenges of implementing an in-beam PET system configuration using partial-ring detectors by providing techniques for reconstructing images from PET data acquired using a partial-ring detector configuration. The reconstruction process is specifically designed to account for the limited angular coverage of the partial-ring detector.

Time-of-flight ("TOF") acquisition techniques can be used to partially reverse the effects caused by limited view angles available for partial-ring detectors; thus, data are preferably acquired using a PET system capable of providing TOF information.

Referring now to FIG. 1, a flowchart is illustrated as setting forth the steps of an example method for reconstructing an image of a subject from limited angle TOF PET data, and for using such an image for verification of an ion beam therapy delivery. The method includes provided limited angle TOF PET data to a computer system for reconstruction, as indicated at step 102. In some embodiments, providing the limited angle TOF PET data can include retrieving such data from a data storage or memory. In some other embodiments, providing the limited angle TOF PET data can include acquiring such data with a PET system, such that the acquired data are provided to a computer system for reconstruction. In both instances, for ion beam verification, the limited angle TOF PET data is preferably acquired very soon (e.g., within a few minutes) after ion beam irradiation has ceased to ensure that short-lived radionuclides can be adequately imaged.

The provided limited angle TOF data are then reconstructed to generate images that depict radionuclide activity levels, as generally indicated at process block 104. The image reconstruction process may include an iterative reconstruction that includes solving an optimization problem that is specifically designed to account for the angular coverage represented by the provided limited angle data.

As one example, image reconstruction can proceed as follows. Let $x=\{x_i\}$ denote the discretized activity image for $i=1, \ldots, N$; let $y_{jt}$ denote the provided limited angle TOF data corresponding to a known TOF measurement along the $j^{th}$ line-of-response ("LOR") with TOF index, t, where $j=1, \ldots, M$ and $t=1, \ldots, T$; and let $P=\{P_{ijt}\}$ denote the TOF system matrix. A log-likelihood function that accounts for the Poisson noise within the measurement can be written as, $$L(x, y) = \sum_{j,t} y_{jt} \ln\left(\sum_i P_{ijt} x_i\right) - \sum_i P_{ijt} x_i. \quad (1)$$

Because the acquired data have a limited angular coverage (i.e., the data have a partial geometry), the system matrix can be specifically designed to account for the limited number of angular views accounted for in the data. As one example, the number of rows in the system matrix can be reduced to the same number of view angles represented by the limited angle data. Thus, the image reconstruction process can include selecting an appropriate reduced angle system matrix, as indicated at step 106. Moreover, by appropriately selecting the TOF resolution and the pattern of view angles used for data acquisition, the amount of information obtained in the TOF PET measurement space can be maximized. An optimal image reconstruction for the measured data can then be designed with based on the reduced angle system matrix selected for the measured data.

In some embodiments, anatomical information about the subject can be used to improve the image reconstruction process. This, the image reconstruction process can include providing an anatomical prior to the computer system, as indicated at step 108. As one example, the anatomical prior can be a medical image (e.g., an image acquired with a computed tomography system or with a magnetic resonance imaging system) that depicts the subject. Subjects undergoing ion beam therapy will routinely have such medical images available for use.

In some instances, the anatomical prior images can be registered to the treatment and in-beam PET imaging space. As an example, an initial PET image can be reconstructed from the limited angle TOF PET imaging data, to which the anatomical prior image can be registered. The initial PET image can be reconstructed, for example, using a Fourier rebinning based reconstruction, such as those described by S. Ahn, et al., in "Optimal Rebinning of Time-of-Flight PET Data," *IEEE Trans Med Imaging*, 2011; 30(10): 1808-1818., and by B. Bai, et al., in "MAP Reconstruction for Fourier Rebinned TOF-PET Data," *Phys Med Biol*, 2014; 59(4): 925-949.

The image reconstruction can proceed as an iterative reconstruction process, as mentioned above and indicated at step 110. As one example, the iterative reconstruction can be a maximum a posteriori ("MAP") reconstruction, which can be defined based on the log-likelihood function of Eqn. (1) as, $$\arg \min_x \{L(x, y) + \eta D(E, F)\}; \quad (2)$$

where D(E, F) is an information theoretic similarity metric that is defined between two random feature vectors, E and F, and η is a parameter that controls the contribution of the similarity metric. As an example, the feature vectors can be extracted as the feature vectors that can be expected to be correlated in the PET image and the anatomical prior image. The $N_s$ feature vectors extracted from the PET and anatomical images can be represented as $e_k$ and $f_k$, respectively, for $k=1, 2, \ldots, N_s$. These feature vectors can be considered as independent realizations of the random vectors, E and F. Mutual information ("MI") can be used as a measure of similarity between the PET and anatomical images.

The reconstructed PET images can then be analyzed for verification of an ion beam therapy, as indicated at step 112. As described above, when used for verification of ion beam therapy, the image reconstruction process will preferably be carried out on limited angle TOF PET data that is acquired very shortly after beam irradiation, such that both short-lived radionuclides and longer-lived radionuclides can be imaged. A report can then be generated to indicate a verification of the beam therapy delivered to the subject, as indicated at step 114. One example of such a verification process is described by X. Zhu and G. El Fakhri in "Proton Therapy Verification with PET Imaging," *Theranostics*, 2013; 3(10): 731-740.

In some embodiments, image reconstruction can alternatively be carried out using a temporal Fourier rebinning based reconstruction, such as those mentioned above. According to the generalized central slice theorem, the two-dimensional ("2D") Fourier transform of an image, $F(\omega_x, \omega_y)$, can be computed from the Fourier transform of the TOF PET data acquired for a single view angle, φ. However, when the TOF resolution is limited, the 2D Fourier transform of the image, $F(\omega_x,\omega_y)$, is effectively computed for a band along the view angle, $\varphi$. As the TOF resolution increases, more area in the 2D space of $F(\omega_x,\omega_y)$ will be covered. Thus, for data acquisitions with higher TOF resolution (e.g., about 100 picoseconds or less), Fourier rebinning reconstructions may provide sufficient image quality for ion beam therapy verification.

Figure 2:
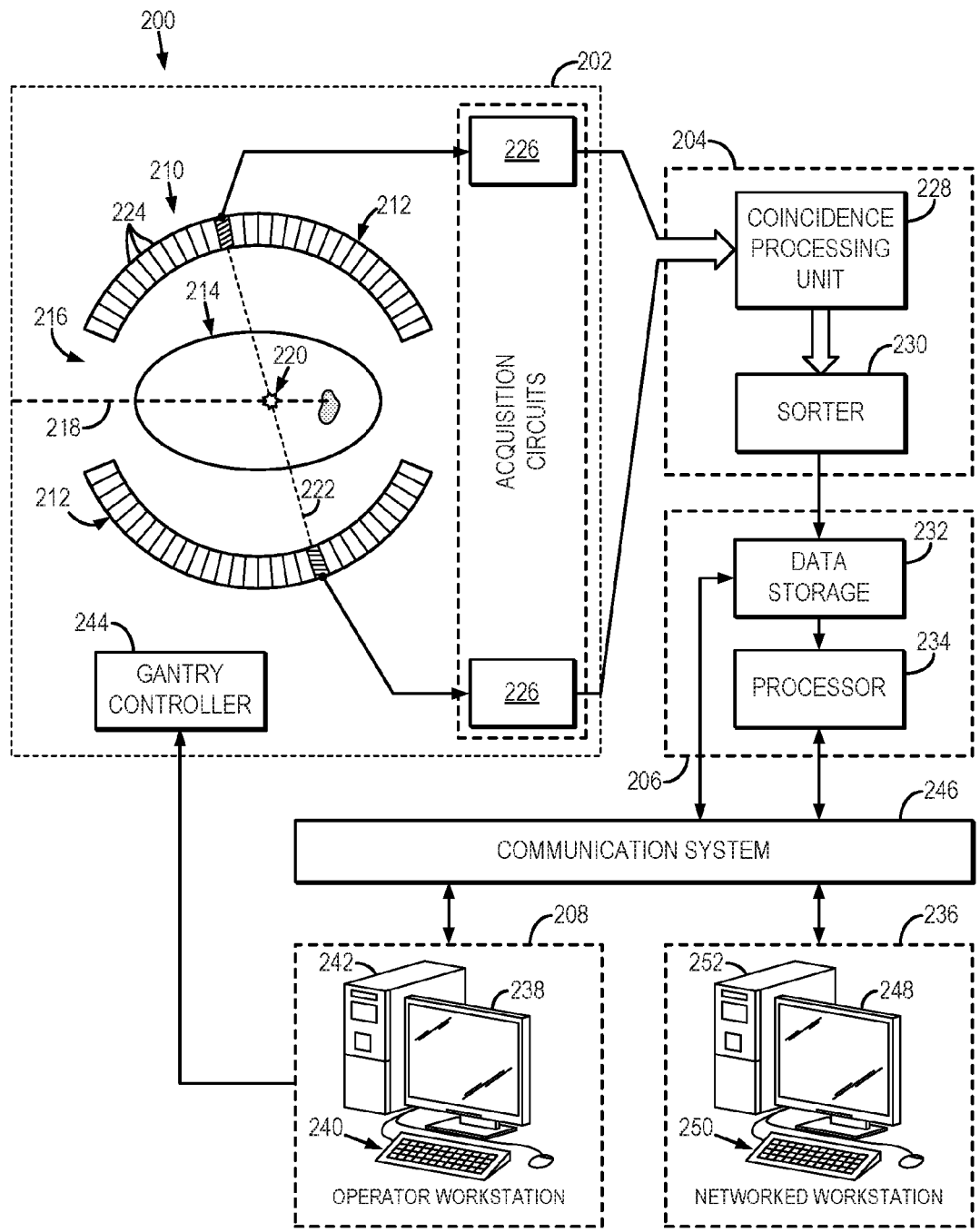
FIG. 2 is a block diagram of an example partial-ring PET system, which can be used to implement the methods described here.

FIG. 2 shows an example of a partial-ring positron emission tomography ("PET") system 200, which can be used as an in-beam PET imaging system for verification of hadron therapies (e.g., proton therapy, carbon beam therapy). The PET system 200 generally includes an imaging hardware system 202, a data acquisition system 204, a data processing system 206, and an operator workstation 208.

The imaging hardware system 202 includes a detector assembly 210 that includes partial-ring detectors 212 that generally define an imaging region into which a subject 214 can be positioned during imaging. The partial-ring configuration of the detector assembly 210 provides an opening 216 through which an ion beam 218 can be delivered to the subject 214. As some non-limiting examples, the opening 216 may correspond to an angular opening of 45 degrees, 60 degrees, or 90 degrees. In general, however, the opening 216 may correspond to an angular opening less than 180 degrees.

The partial ring detectors 212 may be in a dual-head configuration. In some embodiments, the partial-ring detectors 212 can be mounted above and below the patient couch. In some other embodiments, the partial-ring detectors 212 detectors can be mounted on a rotating gantry port.

As mentioned above, the ion beam 218 generates radionuclides along the beam path, and positrons are emitted by these radionuclides as they undergo radioactive decay. These positrons travel a short distance before encountering electrons at which time the positron and electron annihilate. The positron-electron annihilation event 220 generates two photons that travel in opposite directions along a generally straight line 222, which may be referred to as a line-of-response ("LOR").

The partial-ring detectors 212 in the detector assembly 210 include multiple radiation detectors 224. As one example, each radiation detector 224 may include one or more scintillators and one or more photodetectors. Photodetectors that may be used in the radiation detectors 224 include photomultiplier tubes ("PMTs") or avalanche photodiodes ("APDs"). The radiation detectors 224 produce a signal in response to the photons generated by annihilation events 220 that impinge on the radiation detectors 224. The signal responsive to the detection of a photon is communicated to a set of acquisition circuits 226. The acquisition circuits 226 receive the photon detection signals and produce signals that indicate the coordinates of each detected photon, the total energy associated with each detected photon, and the time at which each photon was detected. These data signals are sent to the data acquisition system 204 where they are processed to identify detected photons that correspond to an annihilation event 220.

The data acquisition system 204 may include a coincidence processing unit 228 and a sorter 230. The coincidence processing unit 228 periodically samples the data signals produced by the acquisition circuits 226. The coincidence processing unit 228 assembles the information about each photon detection event into a set of numbers that indicate precisely when the event took place and the position in which the event was detected. This event data is then processed by the coincidence processing unit 228 to determine if any two detected photons correspond to a valid coincidence event.

The coincidence processing unit 228 may determine if any two detected photons are in coincidence as follows. First, the times at which two photons were detected must be within a predetermined time window, for example, within 6-12 nanoseconds of each other. Second, the locations at which the two photons were detected must lie on a line 222 that passes through the field of view in the PET scanner bore. Each valid coincidence event represents the line 222 connecting the two radiation detectors 224 along which the annihilation event 220 occurred, which is referred to as a line-of-response ("LOR"). The data corresponding to each identified valid coincidence event is stored as coincidence data, which represents the near-simultaneous detection of photons generated by an annihilation event 220 and detected by a pair of radiation detectors 224.

In some configurations, the coincidence data may also include time-of-flight ("TOF") information. For example, TOF information may include a difference in the arrival time in the two detectors 224 that measure a coincidence event. This temporal difference can be used to localize the annihilation event 220 along the LOR 222 with an uncertainty $\Delta x=c/\Delta t$, where c is the speed of light and $\Delta t$ is the measured time difference. This localization of the annihilation event 220 along the LOR 222 can also be included in the TOF information.

The coincidence data may be communicated to a sorter 230 where the coincidence events are grouped into projection images, which may be referred to as sinograms. The sorter 230 sorts each sinogram by the angle of each view, which may be measured as the angle of the line-of-response 222 from a reference direction that lies in the plane of the detector assembly 210. For three-dimensional images, the sorter 230 may also sort the sinograms by the tilt of each view. The sorter 230 may also process and sort additional data corresponding to detected photons, including the time at which the photons were detected and their respective energies.

After sorting, the sinograms are provided as limited angle PET data to the data processing system 206 for processing and image reconstruction. The data processing system 206 may include a data storage 232 for storing the raw limited angle PET data. Before image reconstruction, the sinograms in the limited angle PET data can undergo preprocessing to correct for random coincidence events, scatter coincidence events, attenuation effects, and other sources of error. The stored limited angle PET data may thus be processed by a processor 234 located on the data processing system 206, by the operator workstation 208, or by a networked workstation 236.

The operator workstation 208 may include a display 238, one or more input devices 240 (e.g., a keyboard and mouse), and a processor 242. The processor 242 may include a commercially available programmable machine running a commercially available operating system. The operator workstation 208 provides the operator interface that enables scan prescriptions to be entered into the PET system 200. The operator workstation 208 may be in communication with a gantry controller 244 to control the positioning of the detector assembly 210 with respect to the subject 214, and may also be in communication with the data acquisition system 204 to control operation of the imaging hardware system 202 and data acquisition system 204 itself.

The operator workstation 208 may be connected to the data acquisition system 204 and data processing system 206 via a communication system 246, which may include any suitable network connection, whether wired, wireless, or a combination of both.

The PET system 200 may also include one or more networked workstations 236. As an example, the networked workstation 236 may include a display 248, one or more input devices 250 (e.g., a keyboard and mouse), and a processor 252. The networked workstation 236 may be located within the same facility as the operator workstation 208, or in a different facility, such as a different healthcare institution or clinic.

The networked workstation 236 may gain remote access to the data processing system 206 or data storage 232 via the communication system 246. Accordingly, multiple networked workstations 236 may have access to the data processing system 206 and the data storage 232. In this manner, limited angle PET data, reconstructed images, or other data may be exchanged between the data processing system 206 or the data storage 228 and the networked workstations 236, such that the data or images may be remotely processed by a networked workstation 236.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing an image from limited angle positron emission tomography (PET) data, the steps of the method comprising:
   (a) providing limited angle PET data to a computer system, the limited angle PET data indicating gamma ray activity in a subject;
   (b) selecting a reduced angle system matrix that includes rows associated with only view angles represented in the limited angle PET data; and
   (c) iteratively reconstructing the image from the limited angle PET data by iteratively solving an optimization problem that includes the selected reduced angle system matrix.

2. The method as recited in claim 1, wherein the limited angle PET data provided in step (a) includes time-of-flight (TOF) information that localizes annihilation events along a line-of-response.

3. The method as recited in claim 1, wherein the optimization problem includes a maximum a posteriori reconstruction problem based on a log-likelihood function.

4. The method as recited in claim 3, the limited angle PET data provided in step (a) includes time-of-flight (TOF) information that localizes annihilation events along a line-of-response, and the log-likelihood function, $L(x, y)$, is, $$L(x, y) = \sum_{j,t} y_{jt} \ln\left(\sum_i P_{ijt} x_i\right) - \sum_i P_{ijt} x_i;$$

wherein, $y_{jt}$ is the limited angle PET data for the line-of-response, $j$, and TOF index, $t$; $P_{ijt}$ is the reduced angle system matrix; and $x_i$ is the image being iteratively reconstructed.

5. The method as recited in claim 4, further comprising providing an anatomical prior image of the subject to the computer system and constraining the maximum a posteriori reconstruction problem using the anatomical prior image.

6. The method as recited in claim 5, wherein the anatomical prior image includes at least one of a computed tomography image or a magnetic resonance image.

7. The method as recited in claim 5, wherein the maximum a posteriori reconstruction problem is, $$\arg \min_x \{L(x, y) + \eta D(E, F)\};$$

wherein $D(E,F)$ is a similarity metric defined between a first random feature vector, $E$, in the image being iteratively reconstructed and a second random feature vector, $F$, in the anatomical prior image, and wherein $\eta$ is a parameter that controls contributions of the similarity metric.

8. The method as recited in claim 7, wherein the similarity metric is a measure of mutual information between the first and second random feature vectors.

9. The method as recited in claim 1, wherein the limited angle PET data is provided to the computer system by acquiring the limited angle PET data using a PET system having a partial-ring detector that acquired data over a limited number of view angles.

10. The method as recited in claim 9, wherein the limited angle PET data are acquired during a time window following delivery of an ion beam to the subject.

11. The method as recited in claim 10, wherein the time window is about twenty minutes or less.

12. The method as recited in claim 10, wherein the time window is about five minutes or less.

13. The method as recited in claim 10, further comprising performing an analysis on the reconstructed image to verify delivery of the ion beam to the subject and generating a report based on the analysis, wherein the report indicates a verification of the ion beam delivery to the subject.

* * * * *